US00PP31252P2

(12) United States Plant Patent
Hartman

(10) Patent No.: US PP31,252 P2
(45) Date of Patent: Dec. 17, 2019

(54) ***CALADIUM* PLANT NAMED 'BLZ 158-14'**

(50) Latin Name: ***Caladium* X *hortulanum***
Varietal Denomination: BLZ 158-14

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/350,096

(22) Filed: Sep. 25, 2018

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373, 263.1
See application file for complete search history.

*Primary Examiner* — June Hwu
(74) *Attorney, Agent, or Firm* — C. A. Whealy

(57) ABSTRACT

A new and distinct cultivar of *Caladium* plant named 'BLZ 158-14', characterized by its intermediate height; upright and mounding plant habit; dense and bushy appearance; vigorous growth habit and rapid growth rate; fancy-type leaves that are dark green flushed with greyed purple in color with red purple-colored centers and venation; and petioles that are light red to greyed red in color with darker greyed red streaks and stripes.

4 Drawing Sheets

Botanical designation: *Caladium* X *hortulanum.*
Cultivar denomination: 'BLZ 158-14'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'BLZ 158-14'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2008 in Avon Park, Fla. of *Caladium* X *hortulanum* 'Aaron', not patented, as the female, or seed, parent with *Caladium* X *hortulanum* 'Blaze', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2009.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2010 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BLZ 158-14'. These characteristics in combination distinguish 'BLZ 158-14' as a new and distinct *Caladium* plant:

1. Intermediate in height and upright and mounding plant habit; dense and bushy appearance.
2. Vigorous growth habit and rapid growth rate.
3. Fancy-type leaves that are dark green flushed with greyed purple in color with red purple-colored centers and venation.
4. Petioles that are light red to greyed red in color with darker greyed red streaks and stripes.

Plants of the new *Caladium* differ primarily from plants of the female parent, 'Aaron', in the following characteristics:

1. Plants of the new *Caladium* are intermediate in height whereas plants of 'Aaron' are tall.
2. Plants of the new *Caladium* are denser and bushier than plants of 'Aaron'.
3. Plants of the new *Caladium* and 'Aaron' differ in leaf color as leaves of the new *Caladium* are dark green flushed with greyed purple in color with red purple-colored centers and venation whereas leaves of 'Aaron' are mostly white in color with green-colored borders.
4. Plants of the new *Caladium* and 'Aaron' differ in leaf petiole color as petioles of the new *Caladium* are light red to greyed red in color with darker greyed red streaks and stripes whereas petioles of 'Aaron' are green in color.

Plants of the new *Caladium* differ primarily from plants of the male parent, 'Blaze', in the following characteristics:

1. Plants of the new *Caladium* are denser and bushier than plants of 'Blaze'.
2. Plants of the new *Caladium* and 'Blaze' differ in leaf color as leaves of the new *Caladium* are dark green flushed with greyed purple in color with red purple-colored centers and venation whereas leaves of 'Blaze' are dark green in color with burgundy red-colored venation and centers.

3. Leaves of plants of the new *Caladium* are glossier than leaves of plants of 'Blaze'.
4. Plants of the new *Caladium* and 'Blaze' differ in leaf petiole color as petioles of the new *Caladium* are light red to greyed red in color with darker greyed red streaks and stripes whereas petioles of 'Blaze' are mostly tan pink and distally, salmon pink in color.

Plants of the new *Caladium* can be compared to plants of *Caladium* X *hortulanum* 'Frieda Hemple', not patented. In side-by-side comparisons, plants of the new *Caladium* differ primarily from plants of 'Frieda Hemple' in the following characteristics:

1. Plants of the new *Caladium* and 'Frieda Hemple' differ in leaf color as leaves of the new *Caladium* are dark green flushed with greyed purple in color with red purple-colored centers and venation whereas leaves of 'Frieda Hemple' are medium green in color with bright red-colored centers and venation.
2. Leaves of plants of the new *Caladium* are glossier than leaves of plants of 'Frieda Hemple'.
3. Plants of the new *Caladium* and 'Frieda Hemple' differ in leaf petiole color as petioles of the new *Caladium* are light red to greyed red in color with darker greyed red streaks and stripes whereas petioles of 'Frieda Hemple' are tan pink in color.

Plants of the new *Caladium* can be compared to plants of *Caladium* X *hortulanum* 'Postman Joyner', not patented. In side-by-side comparisons, plants of the new *Caladium* differ primarily from plants of 'Postman Joyner' in the following characteristics:

1. Plants of the new *Caladium* and 'Postman Joyner' differ in leaf color as leaves of the new *Caladium* are dark green flushed with greyed purple in color with red purple-colored centers and venation whereas leaves of 'Postman Joyner' are dark green in color with bright red-colored centers.
2. Plants of the new *Caladium* and 'Postman Joyner' differ in leaf petiole color as petioles of the new *Caladium* are light red to greyed red in color with darker greyed red streaks and stripes whereas petioles of 'Postman Joyner' are dark olive green to close to black in color.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'BLZ 158-14' in a container and grown in a shadehouse (tuber de-eyed).

The photograph at the top of the second sheet is a comparison view of typical potted plants of the female parent, 'Aaron' (right), 'BLZ 158-14' (center) and the male parent, 'Blaze' (left).

The photograph at the bottom of the second sheet is a comparison view of typical potted plants of 'Frieda Hemple' (left), 'BLZ 158-14' (center) and 'Postman Joyner' (right).

The photograph at the top of the third sheet is a comparison view of typical plants of 'BLZ 158-14' grown in containers; the plant on the left has not had its tuber de-eyed and the plant on the right has had its tuber de-eyed prior to planting.

The photograph at the bottom of the third sheet is a side perspective view of typical plants of 'BLZ 158-14' grown in an open production field.

The photograph at the top of the fourth sheet is a close-up view of typical freshly-harvested tubers with roots and leaf petioles of 'BLZ 158-14'.

The photograph at the bottom of the fourth sheet is a close-up view of a typical inflorescence of 'BLZ 158-14'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shadehouse were seven weeks old and plants grown in the outdoor nursery were 28 weeks old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'BLZ 158-14'.

Parentage:

*Female, or seed, parent.*—*Caladium* X *hortulanum* 'Aaron', not patented.

*Male, or pollen, parent.*—*Caladium* X *hortulanum* 'Blaze', not patented.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented; individual segments elongated and irregular in shape. Height: About 3.8 cm. Diameter: About 5.9 cm to 9 cm. Segment height: About 2.5 cm to 2.9 cm. Segment diameter: About 1.7 cm to 2.1 cm. Axillary buds size: About 3 mm by 5 mm. Texture: Thick, starchy; somewhat brittle. Color: Epidermis, freshly-harvested: Close to 159C and 176D. Epidermis, dried: Close to 200A. Cortical tissue: Close to 2D. Axillary buds: Close to N155C. Root description: Thick, fleshy contractile roots with few lateral branches; color, close to 155D. Rooting habit: Dense.

Plant description:

*Plant type*.—Herbaceous perennial; suitable as a potted plant in containers 15-cm to 25-cm and suitable as a landscape plant in shaded areas.

*Plant and growth habit*.—Intermediate in height and upright to mounded plant habit; dense and bushy appearance; vigorous growth habit and rapid growth rate; potted plants finish in saleable form in about six to seven weeks after planting tubers; leaf petioles and leaves arise from one or more growing points on tubers; leaf petioles initially upright and outwardly leaning with development.

*Plant height, from soil level to top of foliar plane, shadehouse-grown potted plants*.—About 26 cm to 32 cm.

*Plant height, from soil level to top of inflorescences, shadehouse-grown potted plants*.—About 20.6 cm.

*Plant diameter or spread, shadehouse-grown potted plants*.—About 26 cm to 30 cm.

*Number of shoots per plant, shadehouse-grown potted plants, tubers not de-eyed*.—About two to three develop per #1 tuber.

*Number of shoots per plant, shadehouse-grown potted plants, tubers de-eyed*.—About three develop per #1 tuber.

*Cataphylls, shadehouse-grown potted plants*.—Length: About 5.5 cm to 7 cm. Width: About 1.3 cm. Shape: Wedge-shaped. Apex: Acuminate. Base: Sheathing the stem. Color, inner surface: Close to N155C; colors and patterns on the outer surface are visible on the inner surface. Color, outer surface: Close to 147D and 161D flushed with close to 180C to 180D; stripped and streaked with close to 171A; with development, color becoming closer to 199A to 199B and tinged with close to 187B.

Leaf description:

*Arrangement and type*.—Alternate; simple; fancy-type.

*Length, shadehouse-grown potted plants*.—About 15 cm to 19.5 cm.

*Width, shadehouse-grown potted plants*.—About 9 cm to 11.9 cm.

*Shape*.—Ovate; flat to somewhat concave towards the center.

*Apex*.—Acute to acuminate.

*Base*.—Sagittate to peltate.

*Margin*.—Entire; mostly flat with some broad undulations.

*Texture and luster, upper surface*.—Smooth, glabrous; somewhat glossy.

*Texture and luster, lower surface*.—Smooth, glabrous; glaucous with a dull sheen.

*Venation pattern*.—Pinnate.

*Color, shadehouse-grown potted plants*.—Developing and fully developed leaves, upper surface: Background color: Close to 147A flushed with close to 183A. Leaf edge: Close to 187B. Basal notch: Close to 185A. Midvein and primary venation: Close to 53B and 53C surrounded by close to 47C. Interveinal areas: Close to 181C. Developing and fully developed leaves, lower surface: Background color: Close to 191A tinged with close to 189A. Leaf edge: Close to 187B. Basal notch: Close to 187B. Midvein: Close to 181B streaked with close to 181A and surrounded by close to 182B and 182C. Primary venation: Close to 181D surrounded by close to 38C. Smaller lateral venation: Close to 189A and close to 189A tinged with close to 181C.

*Petioles*.—Aspect: Initially upright and straight and outwardly leaning with development; flexible. Length, shadehouse-grown potted plants: About 16 cm to 23 cm. Diameter, distally, shadehouse-grown potted plants: About 3 mm to 4 mm. Diameter, proximally, shadehouse-grown potted plants: About 5 mm to 7 mm. Texture: Smooth, glabrous. Color, shadehouse-grown potted plants: When developing and fully developed: Close to 39D and 180D streaked with close to 180C and sparsely striped with close to 181A to 181B tinged with close to 177A; proximally, close to 147D and 161D flushed with close to 180C and 180D and streaked and stippled with close to 171A; distally, close to 48C streaked with close to 48A and striped with close to 181A to 181B. Wing length, shadehouse-grown potted plants: About 4.7 cm to 6 cm. Wing diameter, shadehouse-grown potted plants: About 7 mm. Texture and luster, inner and outer surfaces: Smooth, glabrous; slightly glossy. Wing color, shadehouse-grown potted plants: Inner surface: Close to N155C; colors and patterns on the outer surface are visible on the inner surface. Outer surface: Close to 147D and 161D flushed with close to 180C to 180D and stippled, streaked and variably marbled with close to 171A.

Inflorescence description: Inflorescences observed on twelve week-old shadehouse-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring and summer in central Florida; flowers develop about twelve weeks after growth commences; inflorescences last about three days before fading; inflorescences persistent.

*Spathe*.—Length, overall: About 10.2 cm. Length, distal open portion: About 6.7 cm. Length, proximal closed portion: About 3.5 cm. Width, distal open portion: About 3.2 cm. Depth, distal open portion: About 1.6 cm. Width, at constriction: About 1 cm. Width, proximal closed portion: About 2.1 cm. Shape, open portion: Ovate. Apex: Acuminate. Base: Acute. Margin: Entire; smooth; distally, slightly recurved. Texture and luster, front and rear surfaces: Smooth, glabrous; dull, slightly glaucous. Color, front surface: Distal open portion: Close to 155C tinged with close to 145D; towards the margins, close to 145D; with development, color becoming closer to 200C and 199A. Proximal closed portion: Close to 195B and 196B; towards the base, faintly flushed with close to N186C; color does not change with development. Color, rear surface: Distal open portion: Close to 155C with random sectors, close to 145C and 145D; color does not change with development. Proximal closed portion: Close to 147C to 147D, variably streaked and mottled with close to 147D tinged with close to 182D; margin, tinged with close to 54C and 182D; color does not change with development.

*Spadix*.—Length, overall: About 8.1 cm. Length, male flower zone: About 5.1 cm. Length, sterile zone: About 1.6 cm. Length, female flower zone: About 1.4 cm. Diameter, male flower zone: About 7.5 mm. Diameter, sterile flower zone: About 5.5 mm. Diameter, female flower zone: About 8 mm. Shape: Columnar, spindle-shaped. Apex: Acute. Base: Obtuse. Aspect: Upright. Color, mature, male zone: Close to 155D. Color, mature, sterile zone: Close to 155D. Color, mature, female zone: Close to 11D. Male flowers: Quantity per spadix: About 126. Shape: Obovate. Height: About 3.5 mm. Diameter: About 3 mm. Pollen amount: Moderate. Pollen color: Close to 4D. Female flowers: Quantity per spadix: About 120. Shape: Ovate. Height: About 2.5 mm. Diameter: About 2 mm. Stigma color: Close to 11D. Ovary color: Close to 11D.

*Scape*.—Length: About 10.4 cm. Diameter: About 5.5 mm. Strength: Sturdy; flexible. Aspect: Mostly erect. Texture and luster: Smooth, glabrous; slightly glossy. Color: Close to 39D and 180D streaked with close to 180C and sparsely striped with close to 181A to 181B tinged with close to 177A; distally, close to 147D stippled, streaked and striped with close to 200C.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'BLZ 158-14' as illustrated and described.

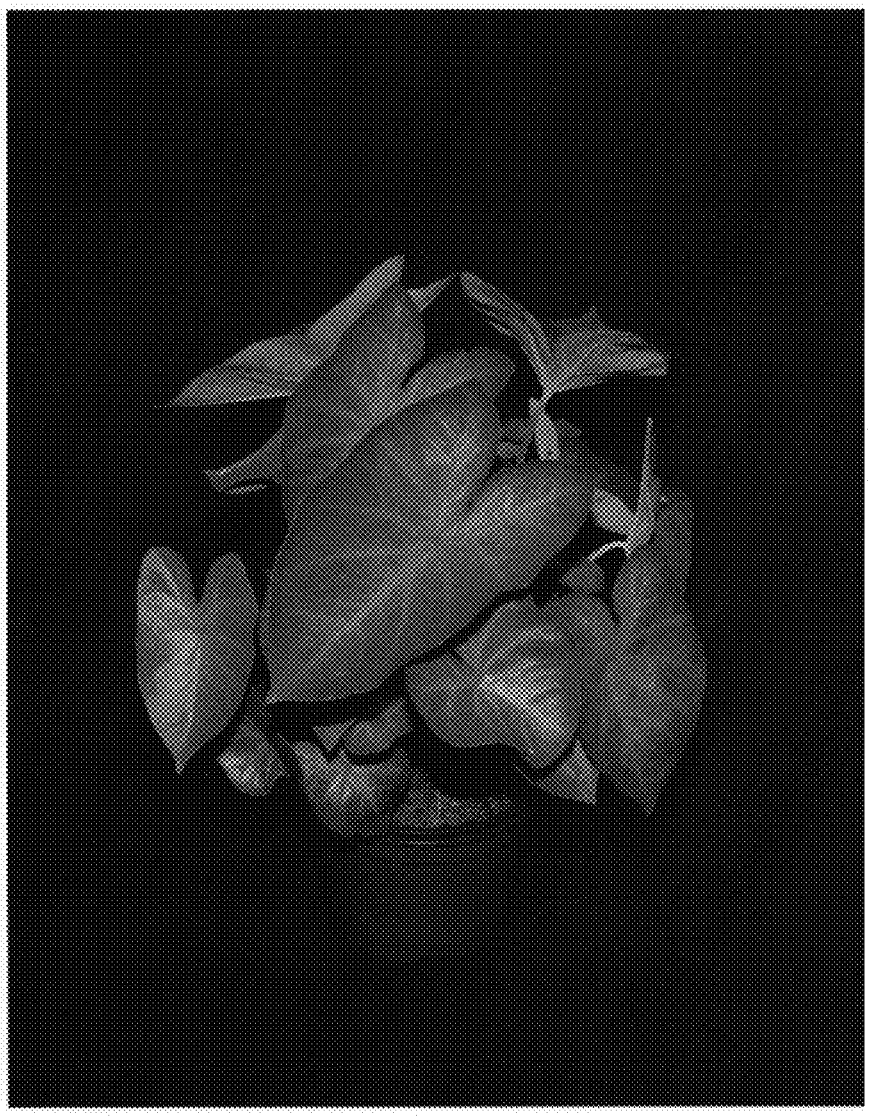

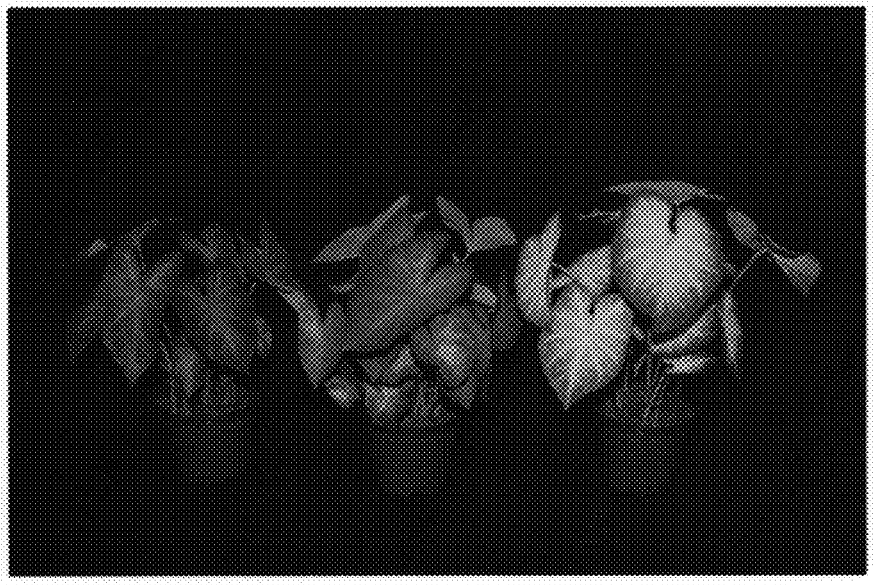
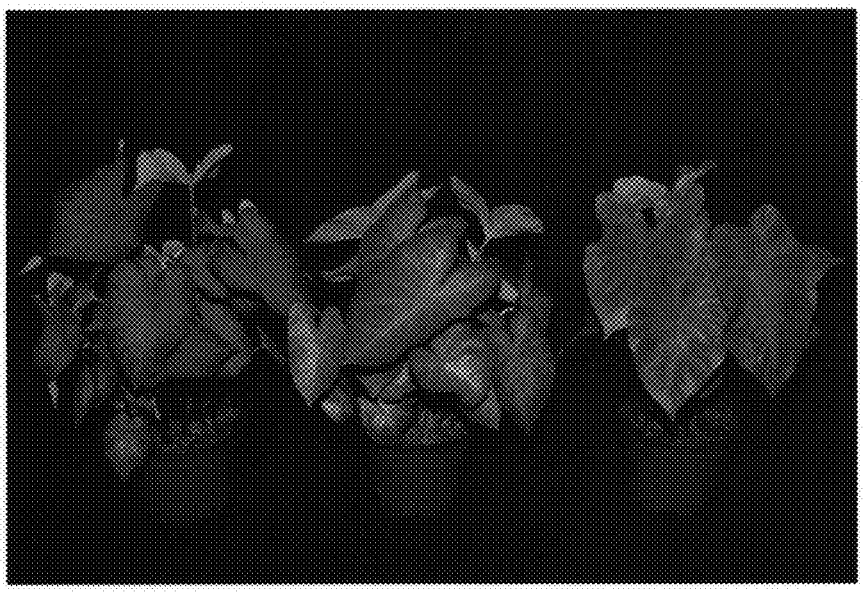

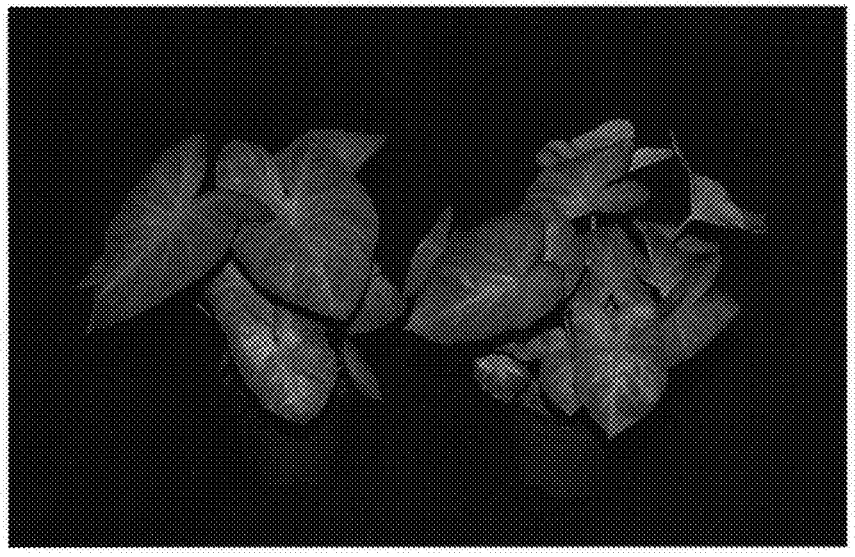
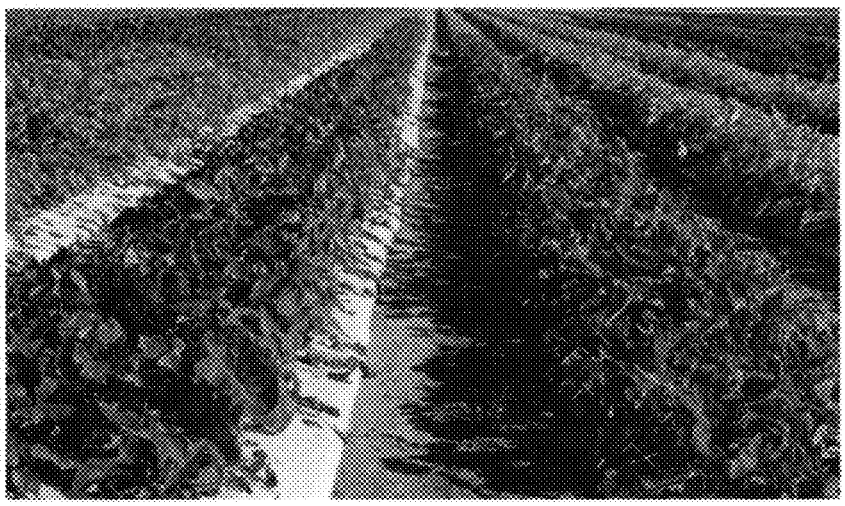

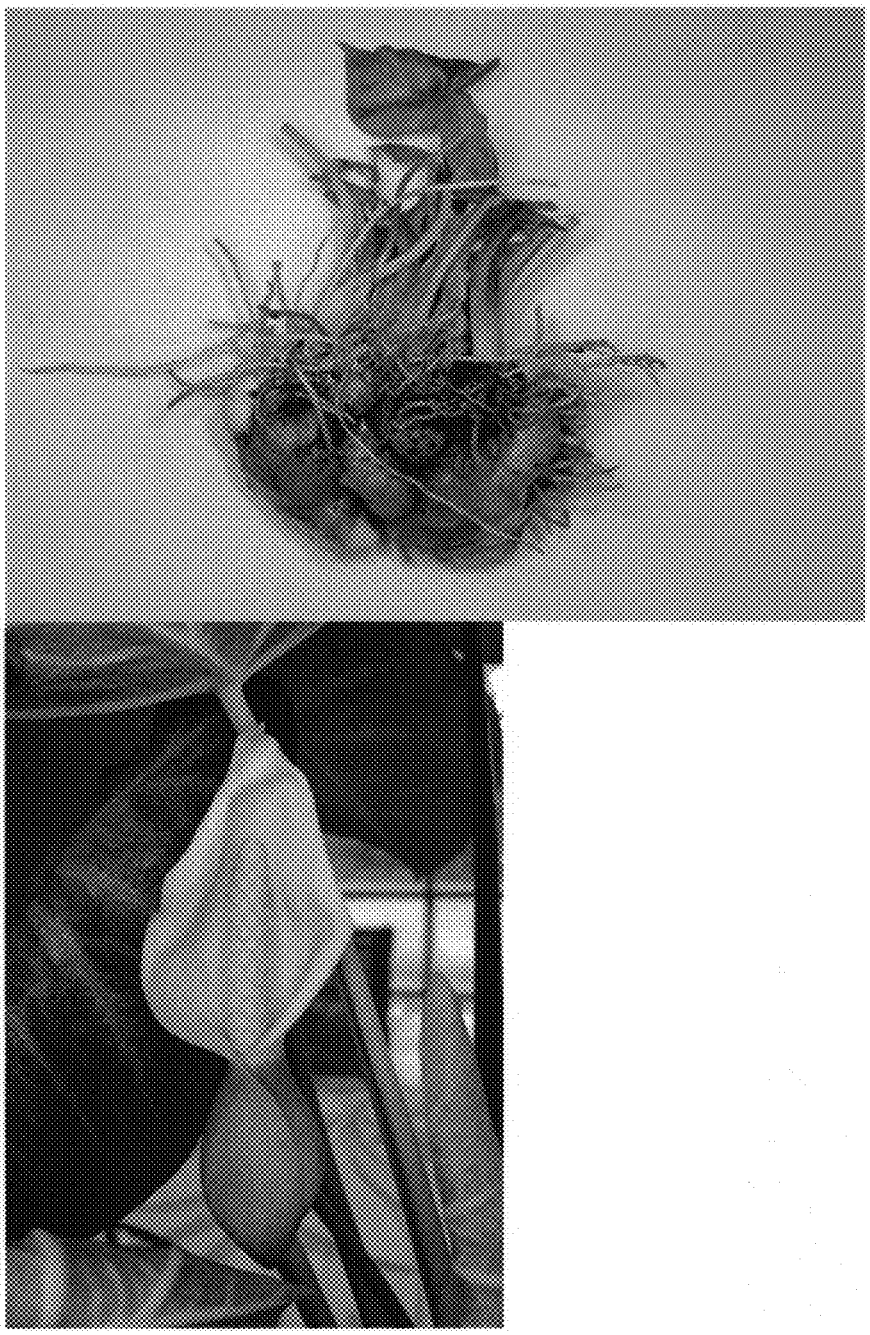

* * * * *